US00RE35152E

United States Patent [19]

Rubin et al.

[11] E Patent Number: Re. 35,152

[45] Reissued Date of Patent: Feb. 6, 1996

[54] METHOD FOR THE DIAGNOSIS AND TREATMENT OF INFLAMMATION

[75] Inventors: Robert H. Rubin, Brookline; H. William Strauss, Newton, both of Mass.

[73] Assignee: The General Hospital Corporation, Boston, Mass.

[21] Appl. No.: 885,835

[22] PCT Filed: Jan. 12, 1987

[86] PCT No.: PCT/US87/00079

§ 371 Date: Nov. 13, 1987

§ 102(e) Date: Nov. 13, 1987

[87] PCT Pub. No.: WO87/04351

PCT Pub. Date: Jul. 30, 1987

Related U.S. Patent Documents

Reissue of:

[64] Patent No.: 4,926,869
Issued: May 22, 1990
Appl. No.: 093,500
Filed: Jan. 12, 1987

U.S. Applications:

[63] Continuation-in-part of Ser. No. 819,585, Jan. 16, 1986, abandoned.

[51] Int. Cl.[6] ..... A61B 5/00

[52] U.S. Cl. ..... 128/654; 424/1.49; 424/9.34; 424/9.341

[58] Field of Search ..... 128/653–654; 424/1.1, 9; 324/309; 436/512–513, 547–548, 113

[56] References Cited

U.S. PATENT DOCUMENTS

| | | | |
|---|---|---|---|
| 4,057,617 | 11/1977 | Abramovici et al. | 424/1 |
| 4,293,537 | 10/1981 | Wong | 424/1.0 |
| 4,315,906 | 2/1982 | Gelder | 429/9 |
| 4,424,200 | 1/1984 | Crockford et al. | 424/1.1 |
| 4,444,744 | 4/1984 | Goldenberg | 128/659 X |
| 4,472,509 | 9/1984 | Gansow et al. | 424/9 X |
| 4,479,930 | 10/1984 | Hnatowich | 424/1.1 |
| 4,636,380 | 1/1987 | Wong | 424/1.1 |
| 4,639,365 | 1/1987 | Sherry | 128/653 X |

FOREIGN PATENT DOCUMENTS

| | | |
|---|---|---|
| 829128 | 9/1975 | Belgium . |
| 832363 | 12/1975 | Belgium . |
| WO85/03231 | 8/1985 | WIPO . |

OTHER PUBLICATIONS

Calame et al., "Detection of a Local Staphylococcal Infection in Mice with Technetium-99m-Labeled Polyclonal Human Immunoglobulin," *J. Nucl. Med.* 32(3):468–474 (1991).

Goedemans et al., "A new, simple method for labelling of proteins with $^{99m}$Tc by derivatization with 1-imino-4-mercaptobutyl groups," in: Technetium and Rhenium in Chemistry and Nuclear Medicine, Nicolini et al. (eds.), Raven Press, N.Y. (1989).

Goodwin et al., "Use of specific antibody for rapid clearance of circulating blood background from radiolabeled tumor imaging proteins," *Eur. J. Nucl. Med.* 9:209–215 (1984).

Physician's Desk Reference, 39th Edition, Medical Economics Co., Inc., pp. 1813–1815 (1985).

Wong et al., "A Rapid Chemical Method of Labeling Human Plasma Proteins with $^{99m}$Tc-Pertechnetate at pH 7.4," *Intl. J. Applied Radiation and Isotopes* 29:251–253 (1978).

Wong, D. W. et al., *Nat'l Journal of Applied Radiation and Isotopes* 28:719–722 (1977).

(List continued on next page.)

*Primary Examiner*—Francis Jaworski
*Attorney, Agent, or Firm*—Sterne, Kessler, Goldstein & Fox

[57] ABSTRACT

The invention relates to a method of detecting an inflammation site in an individual by administering to the individual a diagnostically effective amount of detectably labeled immunoglobulin or fragment thereof, wherein the immunoglobulin substantially accumulates at the site when the site is inflamed.

34 Claims, 7 Drawing Sheets

OTHER PUBLICATIONS

Hoffer, P. et al., "Yearbook of Nuclear Medicine 1984" Yearbook Medl. Publ., Chicago, pp. 211–223.

Reisfeld, R. A. et al., "Monoclonal Antibodies and Cancer Therapy", Alan R. Liss Publ., N.Y. 1985, pp. 215–231.

Thakur, M. L. et al., "Radiolabelled Cellular Blood Elements", Plenum Press, N.Y. ©1985, pp. 274–283, 343–351, 359–361.

Schmidt, J. E., "Atty's Dictionary of Medicine", Binder Publ. N.Y., 1980, vol. 2, p. I–34.

Harrison's *Principles of Internal Medicine* 10th ed., McGraw–Hill, N.Y. ©1983, p. 346.

Mansfield, P. et al., "NMR Imaging in Biomedicine", Academic Press, N.Y. ©1982, p. 234.

METHOD FOR THE DIAGNOSIS AND TREATMENT OF INFLAMMATION

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part of U.S. application Ser. No. 819,585, filed Jan. 16, 1986, now abandoned, which is incorporated by reference herein in its entirety.

BACKGROUND OF THE INVENTION

1. Field of the Invention

This invention is directed to methods of diagnosing inflammation sites in an individual.

2. Description of the Background Art

Inflammation occurs as a consequence of tissue damage. This tissue damage can result from microbial invasion, auto-immune processes, tissue infection, allograft rejection, or such hurtful or destructive external influences as heat, cold, radiant energy, electrical or chemical stimuli, or mechanical trauma. Whatever the cause or bodily site, the inflammatory response is quite similar, consisting of a complicated set of functional and cellular adjustments, involving the microcirculation, fluid shifts, and inflammatory cells (leukocytes). When tissue damage occurs, soluble chemical substances are elaborated which initiate the inflammatory response. The inflammatory response consists of a complex series of events which my be summarized as:

1. A local increase in bloodflow, with capillary dilatation and increased permeability to the fluid components of the blood;

2. A localized exudation of fluid at the site of injury, including the proteins of the plasma that normally leave the capillaries at a relatively low rate;

3. The exudation of leukocytes from the capillaries into the inflammation site. This exudate initially consists primarily of polymorphonuclear leukocytes, followed by monocytes, lymphocytes, and plasma cells. These leukocytes produce a variety of mediators that control the extent and duration of the inflammatory response, and have a series of receptors on their surfaces available to react to the host of chemical medistors and proteins that are part of the inflammatory fluid. Such leukocyte receptor-mediator or protein interactions are important in controlling leukocyte function within the inflammatory site.

The identification and characterization of the sites of inflammation are an important part of medical and veterinary practice. In the case of infectious causes of inflammation, it is frequently necessary to search for "hidden sites of inflammation" in individuals who present with clinical syndromes no more specific than fever and weight loss. Similarly, in patients with auto-immune disease such as rheumatoid arthritis or allograft rejection as causes of inflammation, identification of the site(s) and extent of inflammation and its changes with therapy are an important part of medical and veterinary practice. Not surprisingly, then, much effort has been expended and many techniques developed in an attempt to assess the site(s) and extent of the inflammatory process. These techniques include conventional x-ray techniques, computerized axial tomographic scanning (CAT scanning), and a variety of radionuclide scans. (Sutton, A Textbook of Radiology and Imaging, 3rd Ed., Churchill Livingston, 1980: Clinical Nuclear Medicine, Maysey et al., ed., W. B. Sanders, 1983.) Examples of radionuclide scans which have been utilized are:

1. $^{67}$Gallium, which when injected into an animal or a human binds to the plasma protein transferrin and tends to localize at sites of chronic inflammation.

2. $^{111}$Indium labeled endogenous granulocytes, which when re-injected into the host will tend to accumulate at the site of inflammation; and 3. Radiolabeled chelates which pass into the extracellular fluid and can possibly then accumulate at such sites of fluid accumulation as those associated with inflammation;

4. Thallium scan or so-called first pass radionuclide angiogram to assess areas of increased blood flow.

All of these techniques, on occasion, may provide useful information, but are not adequate because of both false positive and false negative results. A more sensitive and specific means of delineating the anatomical localization of sites of inflammation, particularly one that could be performed serially to assess the response to therapy, is greatly to be desired.

SUMMARY OF THE INVENTION

The present invention relates to a substantially non-invasive method of diagnosing sites of inflammation.

The present inventors have discovered that when immunoglobulins are allowed to contact both inflamed and non-inflamed sites in an individual, they tend to accumulate at the inflamed sites. Further, it was surprisingly discovered that the accumulation at the site of inflammation is not dependent upon the epitopic specificity of the immunoglobulins used. This effect, the concentration of immunoglobulin at the site of inflammation and its use in diagnostic imaging, has not been previously recognized. In other words, non-specific immunoglobulins or mixtures thereof can be used.

The present invention thus relates to an in vivo method of detecting an inflammation site in an individual. This method comprises administering to the individual a detectably labeled immunoglobulin or fragment thereof, wherein the immunoglobulin substantially accumulates at the site when the site is inflamed. Preferably, the immunoglobulin does not substantially accumulate at the site when the site is not inflamed.

Comparative imaging results of three animals with inflammation due to injection of viable bacteria in the left thigh. Each animal was injected with a mixture of three radiolabeled preparations and imaged at various times.

FIGS. 2A–2D: Imaging of inflammation with radiolabeled preparations.

Comparative imaging results of three animals with inflammation due to injection of viable bacteria in the left thigh. Each animal was injected with a mixture of three radiolabeled preparations and imaged at various times.

Figure 1A:
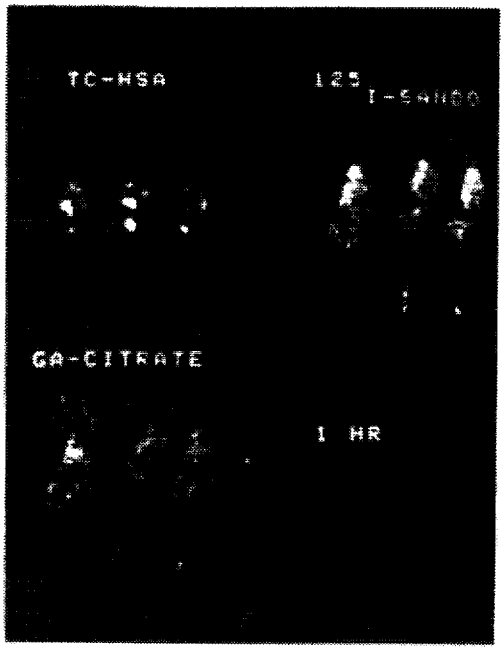
FIGS. 1A–1D: Imaging of inflammation with radiolabeled preparations.
Figure 1B:
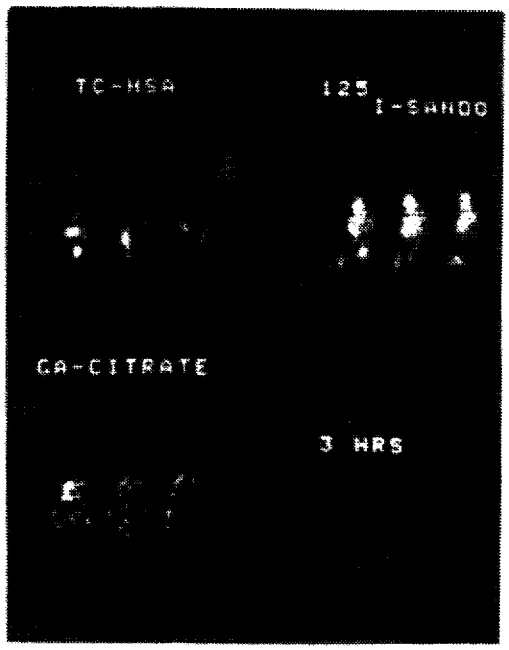
Figure 1C:
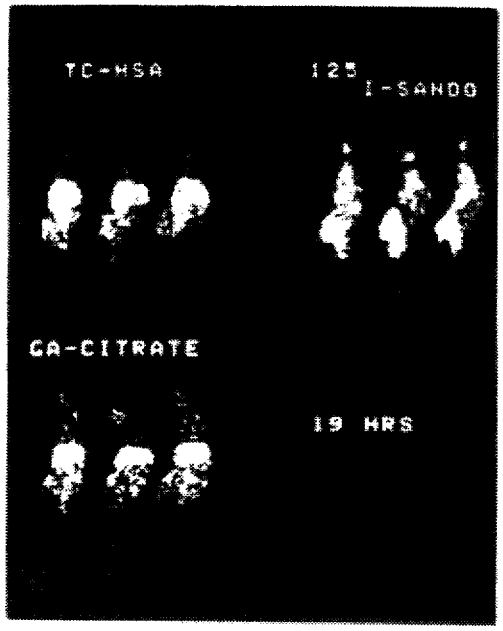
Figure 1D:
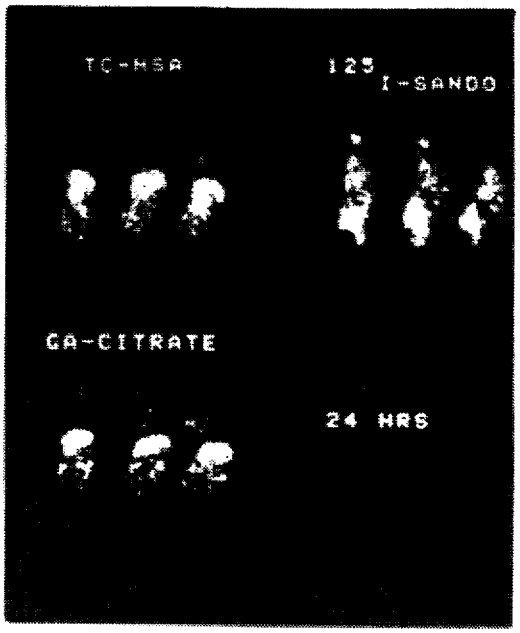
Figure 2A:
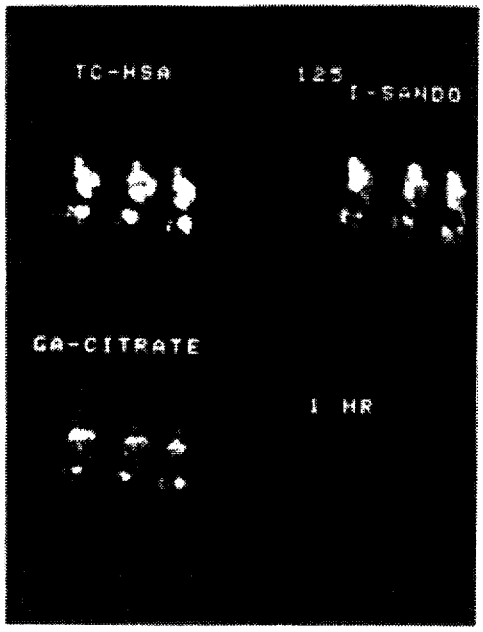
Figure 2B:
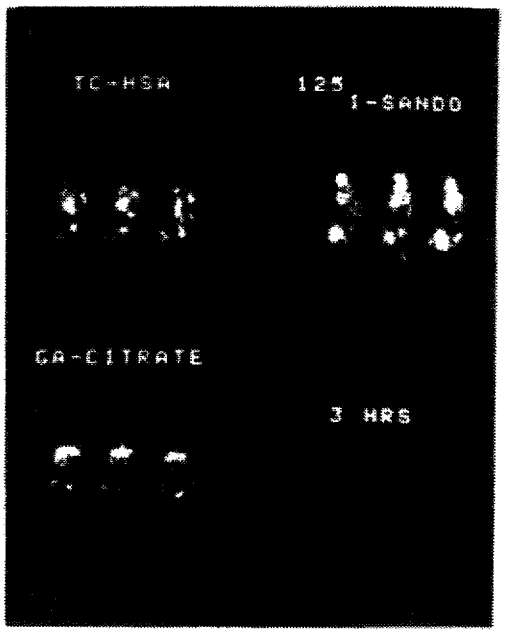
Figure 2C:
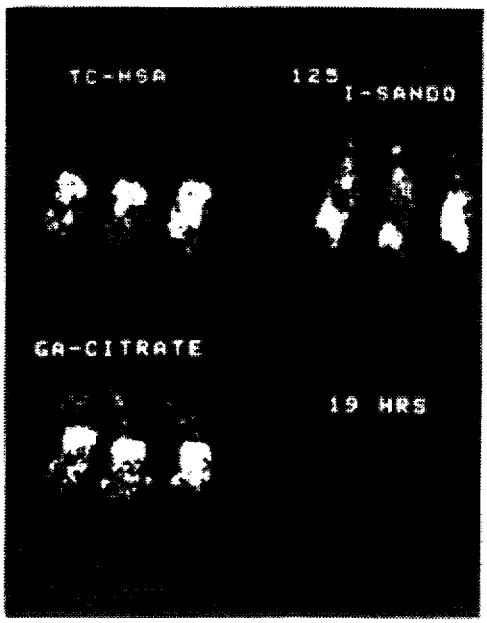
Figure 2D:
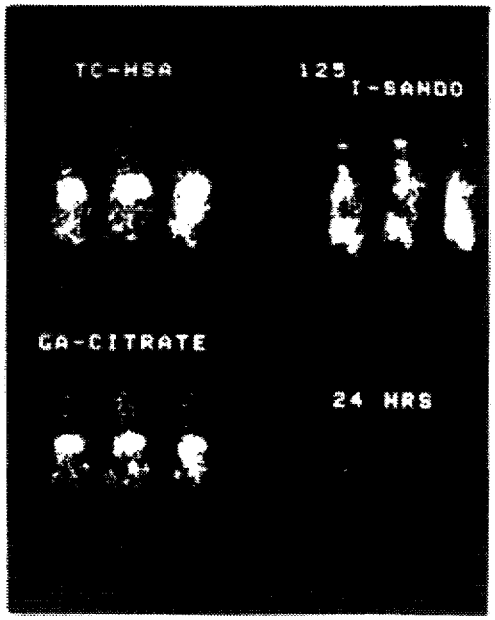
Figure 3:
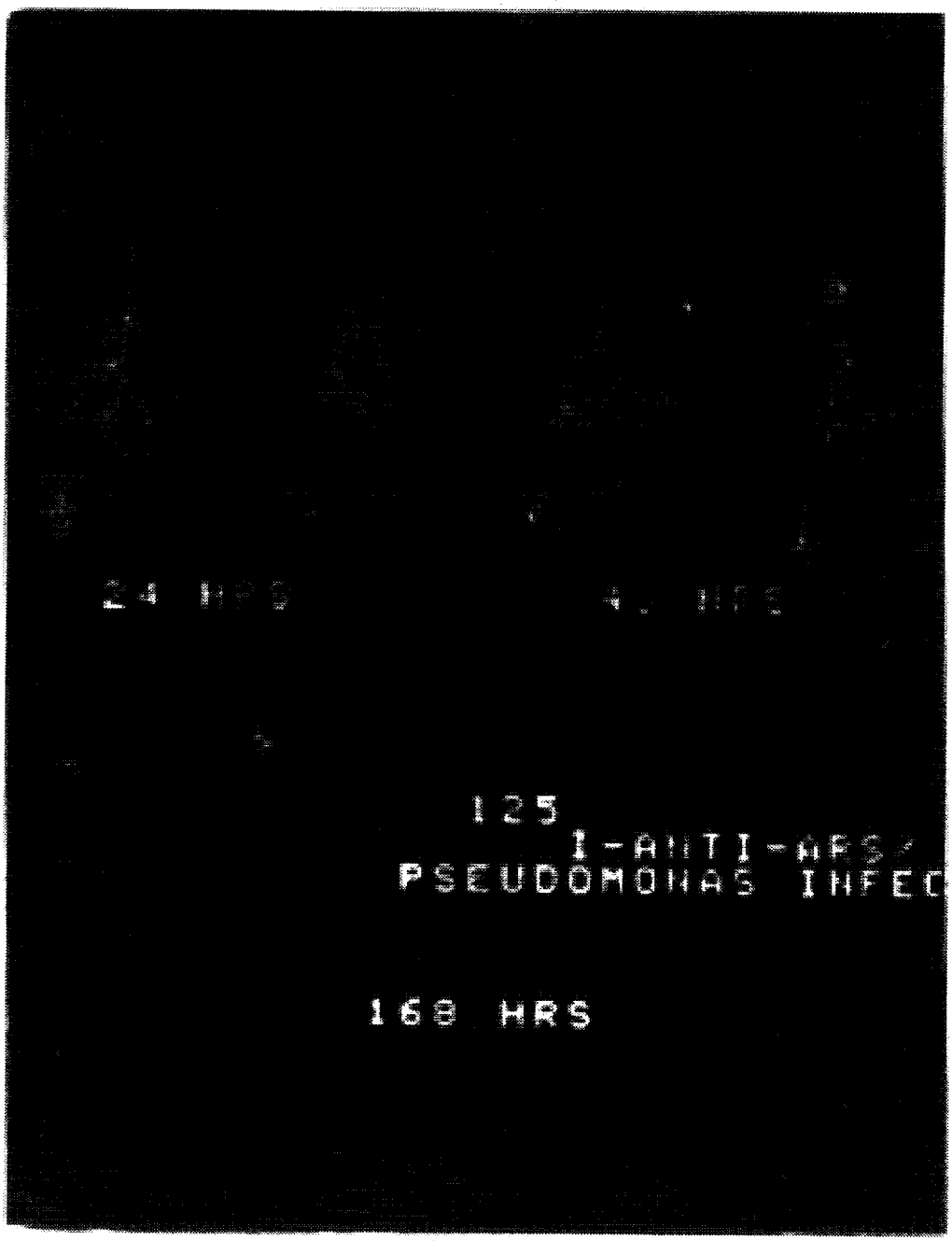

FIG. 3: Imaging of inflammation with non-specific murine immunoglobulin.

This figure shows the kinetics of radiolabeled immunoglobulin in two animals with inflammatory sites in the left thigh due to injection of viable bacteria. Although the inflammation site is clearly detectable at 24 and 48 hours post-injection, the site is no longer detected by 160 hours postinjection.

Figure 4:
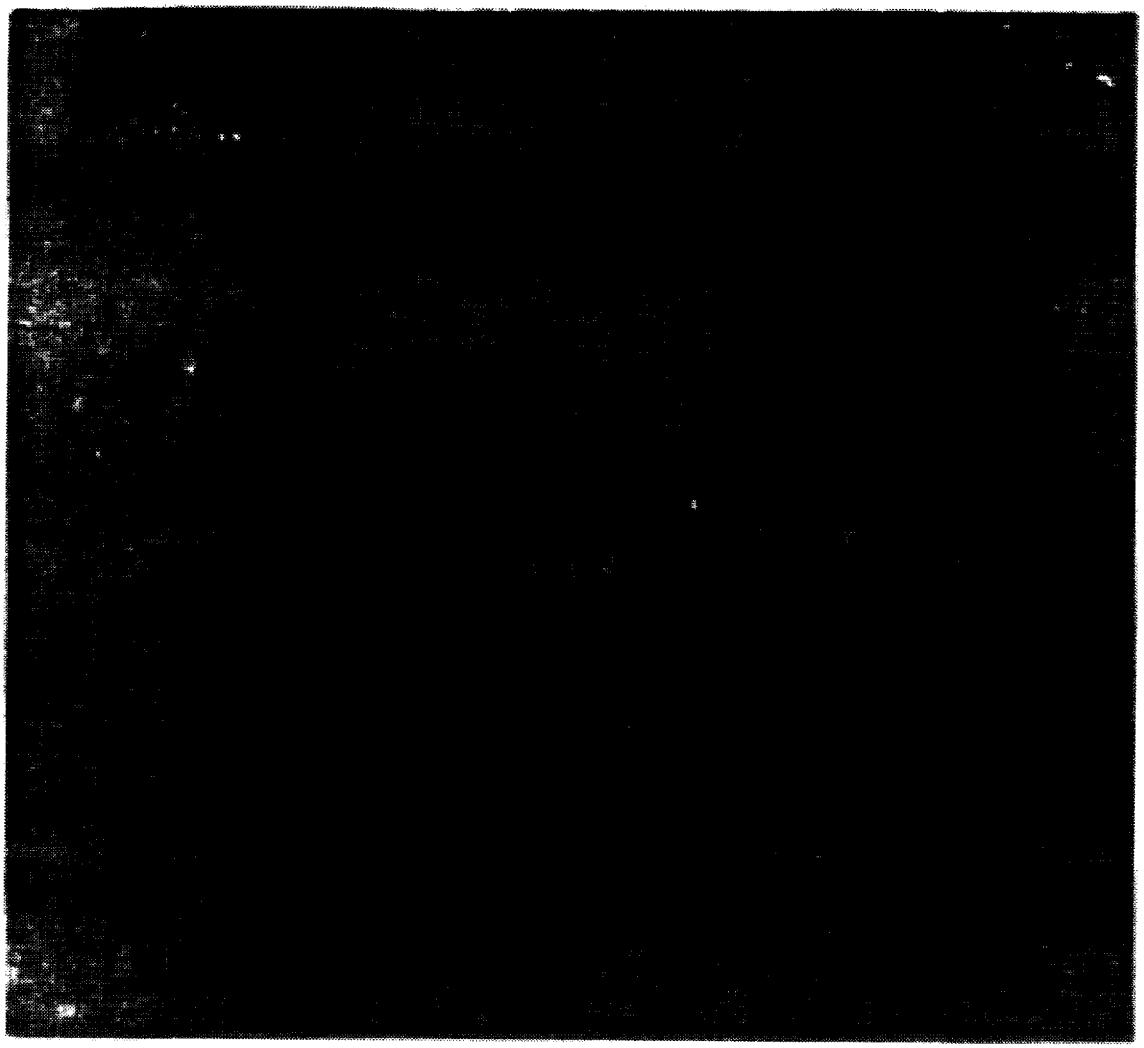

FIG. 4: Imaging of inflammation in human patient.

Immunoglobulin scan of human patient showing localization of mycotic aneurysm in femoral graft.

Figure 5A:
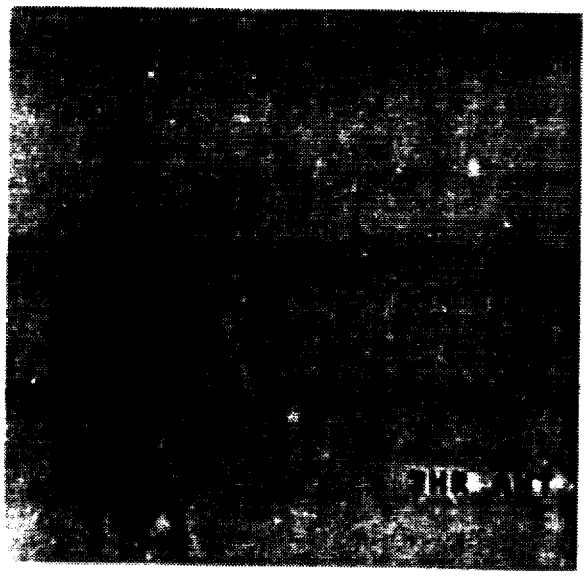
Figure 5B:
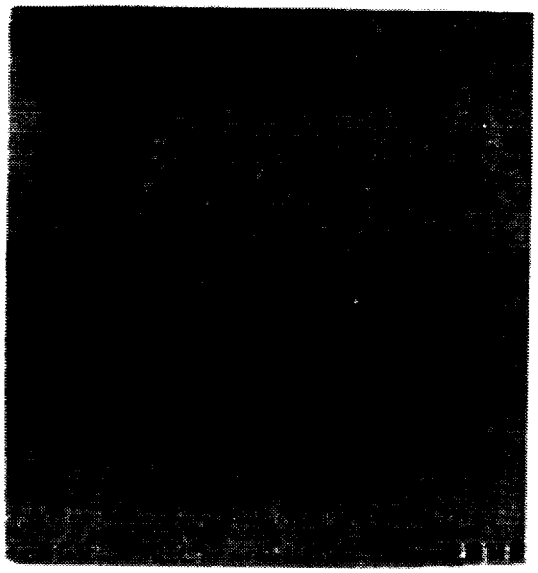

FIGS. 5A–5B: Imaging of inflammation in human patient.

Immunoglobulin scan of human patient indicating a diverticular abscess.

Figure 6A:
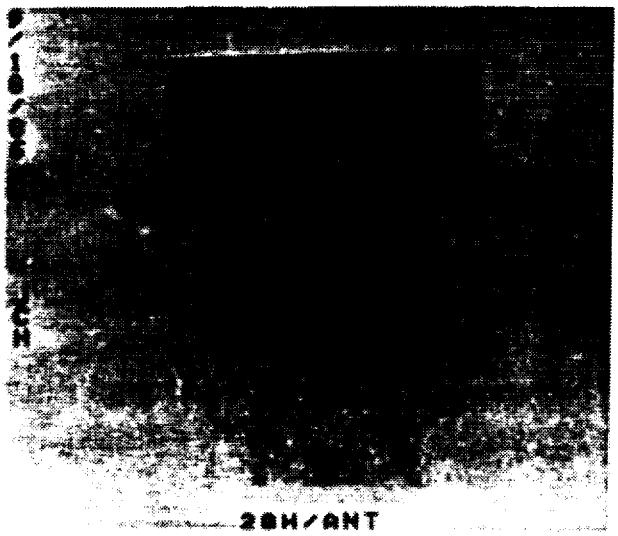
Figure 6B:
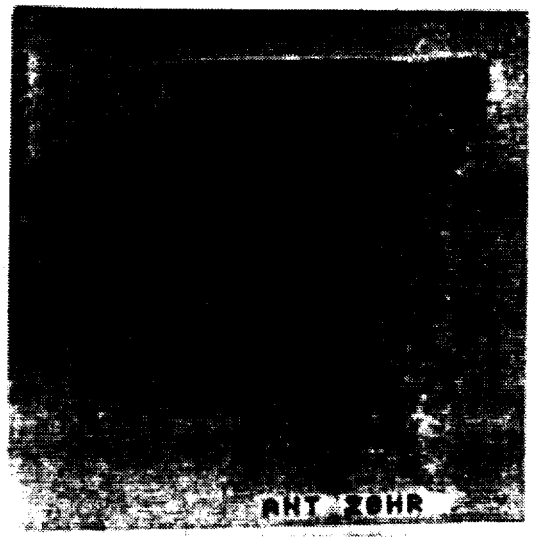

FIGS. 6A–6B: Imaging of inflammation in human patient.

Immunoglobulin scans pre- and post-treatment of human patient with enteritis demonstrating the absence of inflammation after treatment.

Figure 7A:
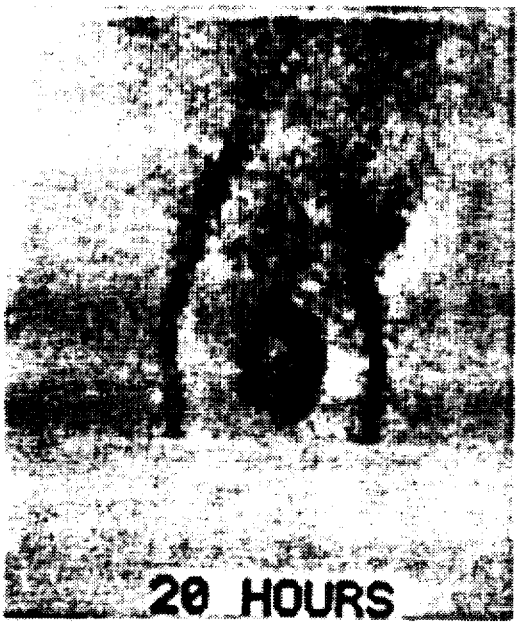
Figure 7B:
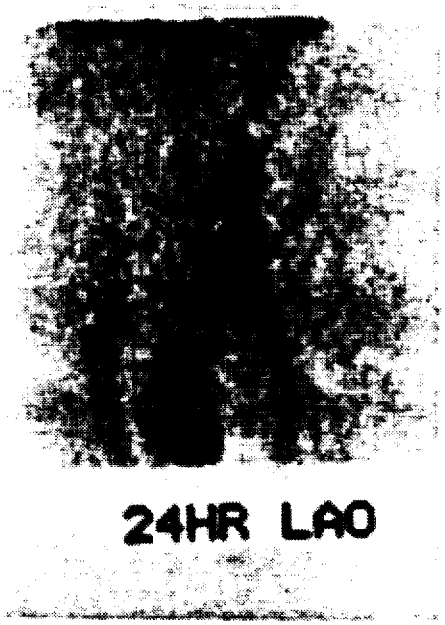
Figure 7C:
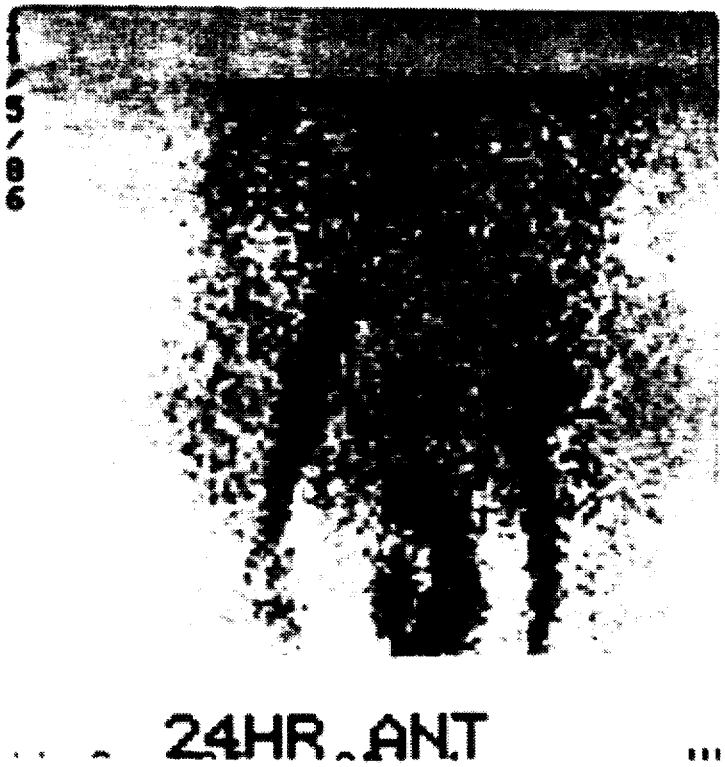

FIGS. 7A–7C: Imaging of inflammation in human patient.

Diagnosis of site of inflammation in groin of human patient by radiolabeled immunoglobulin imaging technique.

DESCRIPTION OF THE PREFERRED EMBODIMENTS

The terms "inflammation" or "inflamed site" are used to denote conditions occurring in an individual due to tissue damage, regardless of the underlying cause or etiology. The concept is more fully described above in the Background Art.

The term "individual" is meant to include both animals and humans.

The immunoglobulins of the invention can be either polyclonally or monoclonally derived, the important factor being that the epitopic specificity of the immunoglobulin used is irrelevant to enable it to localize at the inflammation site.

Polyclonal immunoglobulin preparations can be derived directly from the blood of the desired animal species. Thus, in the case of humans, polyclonal immunoglobulin preparations can be prepared from outdated units of blood utilizing protocols known or readily ascertainable to those of ordinary skill of the art. Such products are commercially available (Sandoz Limited; Cutter Laboratories) and are conventionally used in the treatment of immunodeficiency states, but not in diagnosis. In addition, if desired, polyclonal immunoglobulin preparations may be prepared from the blood of immunized individuals of the desired species following immunization with any of a variety of antigens followed by harvesting of the blood and processing it according to defined techniques. A distinctive advantage of non-specific, polyclonal immunoglobulin preparations is that by preparing immunoglobulin from the same species into which it will be injected, immune reactions across species barriers are prevented and repeated injections of the same product are less likely to cause side-effects. It should be emphasized that crossspecies injections can be done. However, their use might increase the incidence of untoward reactions such as anaphylactic reactions, febrile reactions, and/or the generation of an immune response to the foreign immunoglobulin protein that will block its effective use, as well as endanger the health of the patient. The avoidance of such reactions adds greatly to the appeal of using an immunoglobulin preparation which is from the same species as that being diagnosed.

The nature of the immunoglobulins used is such that they need not have epitopic specificity for the inflamed site, but they nevertheless accumulate substantially at the inflamed site. Thus, immunoglobulin, having essentially any epitopic specificity, will work in the invention.

Monoclonal immunoglobulins which can be used according to the method of the invention can be prepared using hybridoma fusion techniques (Kohler et al., European Journal of Immnunology, 6:292, 1976) or can be derived from known secreting myeloma cell lines such as those available from depositories such as the American Type Culture Collection. As with the polyclonal immunoglobulin preparation, no antigenic or epitopic specificity is needed for the monoclonal immunoglobulin preparation to function effectively in this method. As a consequence, monoclonals of any specificity can be used.

In detecting an in vivo inflammation site in an individual, the detectably labeled immunoglobulin is advantageously given in a dose which is diagnostically effective The term "diagnostically effective" means that the amount of detectably labeled immunoglobulin administered is sufficient to enable detection of the site of inflammation when compared to the background signal.

Generally, the dosage of detectably labeled immunoglobulin for diagnosis will vary depending on considerations such as age, condition, sex, and extent of disease in the patient, counterindications, if any, and other variables, to be adjusted by the individual physician. Dosage can vary from 0.01 mg/kg to 2,000 mg/kg, preferably 0.1 mg/kg to 1,000 mg/kg.

The term "immunoglobulin or a fragment thereof" as used in this invention is meant to include intact molecules as well as fragments thereof, such as, for example, the Fc fragment, which is capable of accumulating at the site of inflammation.

Similarly, the term "Fc portion or part thereof" as used in this invention is meant to include intact Fc fragments as well as portions of the Fc fragment capable of accumulating at the site of inflammation.

The term "diagnostically labeled" means that the immunoglobulin has attached to it a diagnostically detectable label.

There are many different labels and methods of labeling known to those of ordinary skill in the art. Examples of the types of labels which can be used in the present invention include radioactive isotopes and paramagnetic isotopes. Those of ordinary skill in the art will know of other suitable labels for binding to the immunoglobulins used in the invention, or will be able to ascertain such, using routine experimentation. Furthermore, the binding of these labels to the immunoglobulin can be done using standard techniques common to those of ordinary skill in the art.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 keV range, which may be readily detected by conventional gamma cameras.

For in vivo diagnosis, radionuclides may be bound to immunoglobulin either directly or indirectly by using an intermediary functional group. Intermediary functional groups which are often used to bind radioisotopes which exist as metallic ions to immunoglobulins are diethylenetriaminepentaacetic acid (DTPA) and ethylenediaminetetracetic acid (EDTA). Typical examples of metallic ions which can be bound to immunoglobulins are $^{99m}$Tc, $^{123}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl.

The immunoglobulins used in the method of the invention can also be labeled with paramagnetic isotypes for purposes of in vivo diagnosis. Elements which are particularly useful (as in Magnetic Resonance Imaging (MRI) techniques) in this manner include $^{157}$Gd, $^{55}$Mn, $^{162}$Dy, $^{52}$Cr, and $^{56}$Fe.

Alternatively, the method of the invention can be used to monitor the course of inflammation in an individual. Thus, by measuring the increase or decrease in the size or number of inflammatory sites it would be possible to determine whether a particular therapeutic regimen aimed at ameliorating the cause of the inflammatory process, or the inflammatory process itself, is effective.

Another embodiment of the invention includes a method for diagnosing the specific underlying cause of the inflammation at the site. In this method an individual suspected of having an inflammatory site is first administered a diagnostically effective amount of immunoglobulin, as previously described. This detectably labeled immunoglobulin may be of the same or different species as the individual to which it is being administered. The individual suspected of having an inflammatory site is then imaged to determine the presence of a site of inflammation. If the individual is found to have an inflammatory site, the individual is then given an antibody preparation(s) specific for the underlying cause of the inflammation which is suspected. This specific antibody can be from an individual of the same, or a different, species to that of the individual having the inflammatory site. After determining the specific cause of the inflammatory site it is then possible to administer a therapeutic agent, such as therapeutically labeled antibody specific for the underlying cause of the inflammatory process at the inflammation site.

There are distinct advantages to this embodiment of the invention, utilizing the sequential use of non-specific immunoglobulin from an individual of the same species as that suspected of having the inflammatory site, followed by the administration of specific antibody to define and identify the nature of the underlying cause of the inflammatory response. The potential advantages of this sequential strategy include the following:

1. The immunoglobulin preparation used to determine whether any inflammation at all is present is nonsensitizing to the recipient individual since it is from an individual of the same species. Thus, there is little in the way of an adverse allergic or immunologic reaction by the recipient to the immunoglobulin preparation.

2. If the inflammation is not found with the immunoglobulin preparation of 1. above, it is not necessary to administer the detectably labeled specific antibody. Thus, in the situation where detectably labeled specific antibody is unavailable from an individual of the same species as that of the recipient, the recipient will not be exposed to potentially sensitizing amounts of foreign antibody protein. At present, specific antibodies, particularly monoclonal antibodies, are chiefly of murine origin and, thus, may possibly excite an adverse immunologic response in a non-murine recipient. Such adverse immunologic responses limit the number of times a given recipient individual can be exposed to a specific antibody preparation from a different species. Therefore, exposure to such specific antibody of a different species should be restricted to situations of maximum clinical benefit.

The term "therapeutically conjugated" means that a specific antibody used in the just-described preferred method of the invention is conjugated to a therapeutic agent. The therapeutic agents used in this matter act directly upon the underlying cause of the inflammation. Examples of therapeutic agents which can be coupled to the specific antibodies used according to the method of the invention are drugs, radioisotopes, lectins, toxins, and antimicrobials.

Lectins are proteins, usually isolated from plant material, which bind to specific sugar moieties. Many lectins are also able to agglutinate cells and stimulate lymphocytes. Ricin is a toxic lectin which has been used immunotherapeutically. This is accomplished by binding the alpha-peptide chain of ricin, which is responsible for toxicity, to the antibody molecule to enable site-specific delivery of the toxic effect.

Toxins are poisonous substances produced by plants, animals, or microorganisms that, in sufficient dose, are often lethal. Diphtheria toxin is a protein produced by Corynebacterium diphtheriae. This toxin consists of an alpha and beta subunit which, under proper conditions, can be separated. The toxic component can be bound to antibody and used for site-specific delivery to the primary underlying cause of the inflammatory response.

Examples of radioisotopes which can be bound to specific antibody for therapeutic purposes, used according to the method of the invention, are $^{125}$I, $^{131}$I, $^{90}$Y, $^{67}$Cu, $^{217}$Bi, $^{211}$At, $^{212}$Pb, $^{47}$Sc, and $^{109}$Pd.

Anti-microbials are substances which inhibit such infectious microorganisms as bacteria, viruses, fungi, and parasites. These anti-microbials can be any of those known to those of ordinary skill in the art.

Other therapeutic agents which can be coupled to specific antibodies used according to the method of the invention are known, or can be easily ascertained, by those of ordinary skill in the art.

Preparations of the imaging immunoglobulins for parentend administration include sterile aqueous or non-aqueous solutions, suspensions, and emulsions. Examples of non-aqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, and inert gases and the like. See, generally, Remington's Pharmaceutical Science, 16th ed., Mac Eds, 1980.

This invention can be utilized to delineate inflammation at a wide variety of body sites and to diagnose inflammation resulting from a variety of causes such as, but not limited to, infections with parasites, microbes, viruses or fungi; trauma; autoimmune processes; or tumors. The invention is also useful as a means to evaluate the efficacy of, and responses to, therapeutic treatment of inflammation. The diversity of body sites at which inflammation may be identified are exemplified by, but not limited to, muscle, vascular walls, abdomen, groin, and other organ sites.

The above disclosure generally describes the present invention. A more complete understanding can be obtained by reference to the following specific examples which are provided herein for purposes of illustration only, and are not intended to be limiting unless otherwise specified.

EXAMPLE 1

IMAGING OF INFLAMMATION WITH RADIOLABELED PREPARATIONS

Deep thigh inflammation was created in 250 gm Sprague-Dawley rats by the injection of $10^8$ viable, E. coli, Staphylococcus aureus, or Pseudomonas aeruginosa suspended in 0.1 ml of phosphate-buffered saline. Twenty-four hours later, at a time when each animal had clearly evident inflammation of the thigh, each animal was injected via the tail vein with γl ug of a commercially available, intravenous, polyclonal human immunoglobulin preparation (Sandoglobulin®) labeled with 100 uCi of $^{125}$I (Iodogen ®, Pierce Chemical Co., Rockford, Ill.); 100 uCi of $^{67}$Ga; and 65 ug of human albumen labeled with 100 uCi of [$^{99m}$Te] $^{99m}$*Tc*. Thus, each animal was injected with three different isotopes, enabling three different approaches to inflammation imaging to the same animal via a gamma counter. Following injections of these various agents, images were obtained at 1, 3, 19, and 24 hours. FIGS. 1 and 2 illustrate two representative experiments involving three animals in each experiment. Note that the same three animals were imaged at each time point. These images show that there was essentially no imaging of the inflammatory lesion with $^{67}$Ga (considered the standard inflammatory scanning technique); minimal transient imaging with the $^{99m}$Tc labeled albumen; but obvious, increasing visualization of the site of inflammation with the $^{125}$I-labeled polyclonal human immunoglobulin preparation.

In addition to imaging, radioactive counts and count densities were determined over the inflamed site and the non-inflamed contralateral thigh for each isotope at each of the time points of imaging. These values are expressed in Tables 1 and 2 (which correspond to FIGS. 1 and 2, respectively). The same results were observed quantitatively: a transient accumulation at the site of inflammation with albumen; minimal if any accumulation with gallium; and a more sustained, increasing accumulation of labeled immunoglobulin.

TABLE 1*

| Animal/Time | Gallium-67 | $^{125}$I-Immuno-globulin | $^{99m}$Tc-Albumin |
|---|---|---|---|
| #1/1 hr | | | |
| inflamed leg | 740/10 | 1401/19 | 1676/23 |
| uninflamed leg | 372/18 | 670/15 | 626/14 |
| #1/3 hr | | | |
| inflamed leg | 630/8 | 1599/20 | 1200/15 |
| uninflamed leg | 263/4 | 541/8 | 310/5 |
| #1/19 hr | | | |
| inflamed leg | 352/4 | 2443/32 | 887/11 |
| uninflamed leg | 216/3 | 520/8 | 302/4 |
| #1/24 hr | | | |
| inflamed leg | 491/4 | 3507/33 | 580/7 |
| uninflamed leg | 129/2 | 420/6 | 213/3 |
| #2/1 hr | | | |
| inflamed leg | 619/6 | 1809/20 | 1195/20 |
| uninflamed leg | 544/6 | 755/9 | 499/9 |

TABLE 1*-continued

| Animal/Time | Gallium-67 | $^{125}$I-Immuno-globulin | $^{99m}$Tc-Albumin |
|---|---|---|---|
| #2/3 hr | | | |
| inflamed leg | 896/11 | 1985/25 | 1440/18 |
| uninflamed leg | 365/5 | 481/6 | 328/4 |
| #2/19 hr | | | |
| inflamed leg | 1004/5 | 6509/35 | 1286/14 |
| uninflamed leg | 454/5 | 851/9 | 583/9 |
| #2/24 hr | | | |
| inflamed leg | 772/5 | 5130/39 | 819/7 |
| uninflamed leg | 275/2 | 551/5 | 301/4 |
| #3/1 hr | | | |
| inflamed leg | 693/7 | 1791/19 | 2054/23 |
| uninflamed leg | 370/5 | 438/6 | 758/10 |
| #3/3 hr | | | |
| inflamed leg | 831/11 | 1792/24 | 1195/16 |
| uninflamed leg | 238/4 | 319/5 | 273/5 |
| #3/19 hr | | | |
| inflamed leg | 677/5 | 4491/35 | 1014/12 |
| uninflamed leg | 307/3 | 638/7 | 341/3 |
| #3/24 hr | | | |
| inflamed leg | 754/5 | 4148/28 | 897/8 |
| uninflamed leg | 232/3 | 503/6 | 240/3 |

*Date expressed as counts in area of interest (numerator)/count density in counts/pixel (denominator).

TABLE 2*

| Animal/Time | Gallium-67 | $^{125}$I-Immuno-globulin | $^{99m}$Tc-Albumin |
|---|---|---|---|
| #4/1 hr | | | |
| inflamed leg | 937/12 | 2085/27 | 2051/27 |
| uninflamed leg | 290/6 | 633/12 | 599/13 |
| #4/3 hr | | | |
| inflamed leg | 868/11 | 3032/41 | 1853/25 |
| uninflamed leg | 369/11 | 696/10 | 434/6 |
| #4/19 hr | | | |
| inflamed leg | 567/4 | 4576/39 | 1208/13 |
| uninflamed leg | 286/4 | 603/9 | 406/6 |
| #4/24 hr | | | |
| inflamed leg | 638/5 | 4437/36 | 980/7 |
| uninflamed leg | 249/3 | 1262/13 | 385/4 |
| #5/1 hr | | | |
| inflamed leg | 800/12 | 1580/24 | 1556/24 |
| uninflamed leg | 621/7 | 935/10 | 891/10 |
| #5/3 hr | | | |
| inflamed leg | 1025/12 | 2257/28 | 1388/17 |
| uninflamed leg | 282/6 | 575/13 | 357/8 |
| #5/19 hr | | | |
| inflamed leg | 730/6 | 4268/30 | 1300/11 |
| uninflamed leg | 308/3 | 656/7 | 389/4 |
| #5/24 hr | | | |
| inflamed leg | 723/6 | 3226/29 | 755/6 |
| uninflamed leg | 345/4 | 668/8 | 280/3 |
| #6/1 hr | | | |
| inflamed leg | 1315/14 | 2658/29 | 2519/28 |
| uninflamed leg | 226/3 | 369/6 | 385/6 |

TABLE 2*-continued

| Animal/Time | Gallium-67 | $^{125}$I-Immunoglobulin | $^{99m}$Tc-Albumin |
|---|---|---|---|
| #6/3 hr | | | |
| inflamed leg | 1245/12 | 3640/36 | 2353/23 |
| uninflamed leg | 301/5 | 507/8 | 371/6 |
| #6/19 hr | | | |
| inflamed leg | 609/6 | 8161/52 | 1431/17 |
| uninflamed leg | 205/2 | 282/3 | 294/4 |
| #6/24 hr | | | |
| inflamed leg | 702/5 | 7354/50 | 749/9 |
| uninflamed leg | 287/4 | 455/6 | 215/3 |

*Date expressed as counts in area of interest (numerator)/count density in counts/pixel (denominator).

EXAMPLE 2

In other experiments, carried out as in Example 1, $^{111}$In coupled to the human polyclonal immunoglobulin instead of $^{125}$I, yielded excellent images that were brighter and appeared more promptly than did the $^{125}$I-labeled material. This shows that the imaging method is not restricted to a single label.

EXAMPLE 3

A "dose-response" experiment was carried out utilizing 125I-labeled polyclonal human immunoglobulin, in which doses of 65 ug, 650 ug, 5.8 mg, and 122 mg were utilized per animal. The procedures of Example 1 were used. In these experiments, the mount of radioactivity was kept constant (100 uCi), and increasing amounts of "cold" immunoglobulin were added to increase the amount of protein injected. Thus, quantities approximately equivalent to a standard dose, 10× standard, 100× standard, and 1000× standard, were injected. All of these concentrations yielded similar images and similar counts over time, suggesting that the receptors for the immunoglobulin were not saturated even at a 1000× dose schedule. Because of the absence of epitopic specificity of the immunoglobulin preparation used, the accumulation of labeled immunoglobulin at the site of inflammation is not due to conventional recognition of epitopic determinants.

EXAMPLE 4

INFLAMMATION SITE IMAGING USING NON-SPECIFIC MURINE MONOCLONAL ANTIBODY

Deep thigh inflammation was created in Sprague-Dawley rats as previously described above in Example 1. Twenty-four hours later, at a time when each animal clearly evidenced inflammation in the injected thigh, 65 ug of murine monoclonal antibody labeled with 100 uCi of either $^{125}$I or $^{111}$In were injected intravenously via the tail vein. The murine monoclonal antibodies employed in these experiments were of the $IgG_1$ or $IgG_2$ subclass and were of three epitopic specificities. The two epitopic specificities which were used were:

1. $IgG_1$ or $IgG_2$ antibodies directed against an arsenate hapten not found in mammalian species or bacteria.

2. $IgG_1$ antibodies specific for lipid A of E coli.

In these experiments, the anti-arsenate monoclonal antibodies were injected into animals having either E. coli, S. aureus, or P. aeruginosa infection. The anti-E. coli monoclonal antibody was injected into animals bearing staphylococcal or Pseudomonas infection.

All of these labeled immunoglobulin preparations gave similar results. In all animals there appeared an image 1–4 hours post-injection, which peaked in intensity 24–48 hours post-injection, and disappeared completely by 96–120 hours. A representative experiment utilizing the $IgG_1$ anti-arsenate antibody in an animal with a Pseudomonas infection is shown in FIG. 3.

These studies demonstrate that a wide variety of non-specific monoclonal immunoglobulins can be used in this method.

EXAMPLE 5

COMPARISON OF NON-SPECIFIC IMMUNOGLOBULIN IMAGING TO SPECIFIC ANTIBODY IMAGING

Pseudomonas aeruginosa Type I deep thigh infection in Sprague-Dawley rats was created as described above. Twenty-four hours later, 0.65 ug of $^{125}$I-labeled monoclonal antibodies of one of two possible antigenic specificities were injected intravenously via the tail vein. Half of the animals were injected with a murine monoclonal $IgG_1$ antibody specific for Type I P. aeruginosa. The remaining animals were injected with murine monoclonal $IgG_1$ antibody specific for arsenate hapten which is an antigen not found in mammalian tissues or bacteria. The anti-arsenate antibody is thus a control preparation with no epitopic specificity for this animal model. Serial images were taken with the gamma camera at 1, 4, 24, 48, 72, 96, 120, 144, and 168 hours after injection of the radiolabeled monoclonal antibodies. In the first twenty-four hours the images obtained with the specific and non-specific antibodies were identical with images appearing as early as 1–4 hours post-injection. However, beginning at 48 hours, the non-specific (antiarsenate) image began to fade, and had totally disappeared by 72–96 hours. In contrast, the specific (anti-P. aeruginosa) image continued to increase in intensity, peaking at 96–120 hours, and not disappearing until 166 hours had elapsed. Thus, it is possible to differentiate between the non-specific accumulation of immunoglobulin at an inflammation site from the reaction of specific antibody with the underlying cause of the inflammatory response, by following the persistence of the image with time. Specific antibodies remain at the inflammation site longer.

EXAMPLE 6

INFLAMMATION SITE IMAGING USING IMMUNOGLOBULIN FRAGMENT

Deep thigh inflammation was created in Sprague-Dawley rats as described in Example 1 above. After 24 hours when each animal had clear evidence of inflammation, they were injected with 65 ug of either $^{125}$I-labeled Fc fragment (100 uCi), $^{125}$I-labeled Fab fragment (100 uCi), or $^{125}$I-labeled polyclonal human immunoglobulin (100 uCi, Sandoglobulin®). The immunoglobulin fragments were derived from a polyclonal human immunoglobulin preparation (Sandoglobulin®) using standard techniques. The animals were then scanned using a gamma camera as described in Example 1. It was found that while the labeled Fc fragments and labeled immunoglobulins gave similar results, both of these preparations gave considerably stronger and more sustained images than the images produced by the labeled Fab fragments. This finding further supports the fact that accumulation of immunoglobulin at the site of inflammation is unrelated to the epitopic specificity of the immunoglobulin since the Fc fragment has no epitopic binding capability.

EXAMPLE 7

Commercially available polyclonal intravenous human immunoglobulin preparations marketed by Sandoz, Cutter, and Hyland (all licensed as therapeutic preparations) can be utilized interchangeably as imaging reagents. Localized inflammation was produced in 200 gram Sprague-Dawley rats by the injection of $10^8$ E. coli into the left back thigh. Twenty-four hours later, 0.25 mg/kg of the test immunoglobulin preparation, labeled with iodide-125 by the Iodogen® bead technique (100–150 uCi) was injected intravenously. Serial images were then taken 4, 24, and 48 hours post-injection of the radiolabeled immunoglobulin with a gamma camera. In all cases with each of the immunoglobulin preparations, an image of the site of inflammation was seen 4 hours post-injection, with an image of increasing intensity observed 24 hours post-injection. There was no difference in the images achieved with the different immunoglobulin preparations with this method of applying a radiolabel. When indium-111 is utilized as the radiolabel after coupling of diethylenetriaminepentaacetic acid to the immunoglobulin, the Hyland and Sandoz immunoglobulin preparations yield distinctly better images than does the Cutter preparation. These results indicate that the imaging method is effective with immunoglobulins from various sources and utilizing different radionuclides.

EXAMPLE 8

The non-specific immunoglobulin scan can be utilized in a variety of inflammatory states such as those due to a variety of infectious agents or the non-infectious inflammatory agent turpentine. In each of these studies, approximately $10^8$ organisms, or 0.5 cc of turpentine, was injected into the thigh of 100 gram Sprague-Dawley rats. Twenty-four hours later, 0.25 mg/kg of a polyclonal intravenous human immunoglobulin preparation (in all these studies the Sandoz preparation Sandoglobulin® was used) labeled with either $^{125}$I or $^{111}$In, as previously described, was injected intravenously. Images were taken with a gamma camera 4, 24, and 48 hours later. Inflammation was induced in these studies by E. coli, Klebsiella pneumoniae, Staphylococcus aureus, candida albicans, Pseudomonas aeruginosa, Bacteriodes fragilis, or turpentine. In all cases, imaging was observed, commensurate with the degree of inflammation present, as early as 4 hours post-injection and with intensifying images observed 24–48 hours post-injection. These results, utilizing a non-microbial form of inflammation, different classes of bacteria, and a fungus, demonstrate that this technique is truly non-specific and capable of diagnosing inflammation resulting from diverse causes.

EXAMPLE 9

The non-specific immunoglobulin scan can detect inflammation at different anatomical sites.

a. Unilateral nephrectomies were carried out in two groups of rats. In one group, the operation was done sterilely. In the other group, the nephrectomy sites were inoculated with $10^8$ E. coli. Both groups of animals were injected with $^{111}$In-labeled Sandoglobulin® 48 hours later, with serial scans then carried out with the gamma camera. In every instance, scans taken 24 hours post-injection could clearly distinguish sterile post-operative surgically induced inflammation from deep surgical wound infection.

b. Intra-abdominal abscesses were created with Bacteriodes fragilis or mixed bowel bacteria according to standard methods. Approximately 7–10 days later, $^{111}$In-labeled Sandoglobulin® was administered intravenously and serial images obtained with the gamma camera. In each instance, the scans demonstrated the site of the intra-abdominal abscess.

c. Pneumocyctis carinii pneumonia is an opportunistic pneumonia observed in immunocompromised patients, particularly those with AIDS. Early diagnosis, and assessment of response to therapy, particularly in those patients with equivocal chest x-ray, is an important clinical need. Model Pneumocyctis pneumonia was created in rats by placing them on a protein-deficient diet and treating them with daily cortisone and tetracycline for two months. This resulted in the development of Pneumocyctis pneumonia. At a time when these animals' chest x-rays and gallium scans (the current technique employed clinically) were negative, but pathology revealed clear-cut Pneumocystis pneumonia, the $^{111}$In-Sandoglobulin® scans were positive 24–48 hours post-injection. When these animals were treated with effective anti-Pneumocystis therapy (trimethoprim-sulfamethoxazole) repeat scans improved, commensurate with the pathologic evidence of improvement in the pneumonia. These results indicate the usefulness of the method of the present invention to monitor the response of the individual to treatment.

EXAMPLE 10

Anti-inflammatory therapies do not influence the utility of this scanning technique. Groups of animals were pre-treated for 5–7 days with one of the following anti-inflammatory regimens: methylprednisilone, 5 mg IP daily; indomethacin 10 mg/kg/day IV; and acetylsalicylic acid administered in the drinking water to achieve a blood level of 15–25 mg/liter (therapeutic levels used in treatment of humans with rheumatoid arthritis). Model thigh infection was then created with E. coli as described in Example 1, and 24 hours later (while the anti-inflammatory therapy was continued) $^{111}$In-labeled Sandoglobulin® was injected intravenously, with serial scans then carried out. These studies showed no significant effect of the anti-inflammatory treatment on the images obtained.

EXAMPLE 11

The Fab and Fc studies described in Example 6 above were repeated utilizing model infection created with either E. coil or Klebsiella pneumoniae. In every instance, the Fab fragment gave no images, whereas the Fc fragment gave images similar to those obtained with immunoglobulins. These results were identical to those seen in Example 6.

EXAMPLE 12

Radiolabeled non-specific human immunoglobulin was used to image localized inflammation in 15 human patients. There were no false positives or negatives. The technique has proven to be useful in diagnosing intramuscular infection, skeletal infection, and intra-abdominal and pelvic infection. In all these studies, a single polyclonal human immunoglobulin preparation has been employed, Sandoglobulin®, labeled with $^{111}$In after coupling with diethylenetriaminepentaacetic acid by the carboxy-carbonic anhydride method (Krejcarek and Tucker, Biochem. and Biophys. Res. Commun. 77:581–585 (1977)). A dose of 1.9 mCi/patient was administered intravenously with several images carried out over the 24 hours post-injection. It should be noted in all these studies that $^{111}$In non-specifically accumulates in the liver and kidney. This is a function of the indium label, not the immunoglobulin, as shown by animal studies in which iodine-labeled immunoglobulin does not accumulate in the liver whereas indium-labeled immunoglobulin does.

EXAMPLE 13

A 62-year-old woman with extensive vascular disease underwent a left femoral artery-inferior tibial artery bypass graft on 10/31/86; on 11/18/86 she underwent a right femoral-popliteal arterial bypass graft; and on 12/2/86 a thrombectomy of the right femoral artery. Over the next two weeks, she had a low-grade fever, with minimal findings at her operative site. On 12/16/86, she underwent an immunoglobulin scan which revealed a clear-cut accumulation in the lower portion of her right femoral graft (FIG. 4) of radiolabeled immunoglobulin 6 hours post-injection of the reagent. Emergency exploration of this site that evening revealed a mycotic aneurysm of her graft. This was removed, and grew Pseudomonas aeruginosa. In this instance, the scan provided life-saying information non-invasively with no side effects. The results demonstrate the effectiveness of immunoglobulin imaging to diagnose and localize inflammation in the vascular wall.

EXAMPLE 14

A middle-aged woman presented with fever, lower abdominal pain, and a palpable mass on rectal examination. A computerized tomographic (CT) study of her abdomen revealed no abnormality. An immunoglobulin scan revealed a clear-cut accumulation of radiolabeled immunoglobulin in the lower abdomen as early as 3 hours post-injection (FIG. 5). Surgical exploration revealed a large diverticular abscess at the anatomical site outlined by the immunoglobulin scan.

EXAMPLE 15

A middle-aged man with longstanding regional enteritis presented with fever and tenderness in his right upper quadrant just below his liver. CT study was non-diagnostic. Initial immunoglobulin scan demonstrated an inflammatory mass just below his liver (FIG. 6a) corresponding to the site of pain. He was treated with steroids and broad-spectrum antibiotics with resolution of his symptoms. At the completion of therapy, a repeat immunoglobulin scan revealed no remaining area of inflammation (FIG. 6b). Therapy was stopped, and the patient remained well. This result demonstrates that immunoglobulin imaging is effective not only as a diagnostic tool but also to determine the efficacy of treatment.

EXAMPLE 16

A middle-aged man presented in mid-July 1986 with a left groin mass, fever, and chills of 3–4 days' duration. On 7/12/86, he underwent percutaneous drainage of the groin mass, which yielded purulent material that grew small amounts of mixed bowel flora. He was treated with 7 days of intravenous cefazolin therapy. The initial immunoglobulin scan on 7/16/86 revealed a residual inflammatory mass (FIG. 7a). No further therapy was carried out. The patient continued to drain purulent material from his left groin and to experience discomfort for the next four months. A repeat immunoglobulin scan on 11/5/86 revealed a more extensive inflammatory mass in the same area (FIG. 7b). Subsequent surgical exploration revealed an extensive inflammatory mass extending from the sigmoid colon into the groin and up into the retroperitoneum. Thus, the immunoglobulin imaging technique is also effective in following the course of inflammation over a prolonged period.

What is new and is desired to be covered by letters patent is:

1. A method of detecting an inflammation site in vivo in an individual which comprises:

(a) administering to said individual a diagnostically effective amount of [a] *an* agent wherein said agent [consists essentially of] *comprises* a detachably labeled immunoglobulin or [a] *an Fc* fragment *or subfragment* thereof, and said immunoglobulin, *or Fc fragment or subfragment thereof,* substantially accumulates at said site when said site is inflamed *and said agent has no substantial epitopic specificity for said inflamed site* [,]; and (b) detecting said [detectably labeled immunoglobulin] *agent.*

2. The method of claim 1 wherein said [immunoglobulin] *agent* does not accumulate at said site when said site is not inflamed.

3. The method of claim 1 wherein said [immunoglobulin] *agent* is [monoclonally derived] *one or more detectably labeled monoclonal antibodies.*

4. The method of claim 1 wherein said [immunoglobulin] *agent* is [polyclonally derived] *detectably labeled, pooled, human immunoglobulin.*

5. The method as in any one of claims 1–4, wherein said detectable label is a radioactive isotope.

6. The method of claim 5, wherein said isotope is selected from the group consisting of $^{99m}$Tc, $^{123}$I, $^{131}$I, $^{111}$In, $^{97}$Ru, $^{67}$Cu, $^{67}$Ga, $^{68}$Ga, $^{72}$As, $^{89}$Zr, and $^{201}$Tl.

7. The method as in any one of claims 1–4, wherein said detectable label is a paramagnetic label.

8. The method of claim 7, wherein said paramagnetic label is selected from the group consisting of $^{157}$Gd, $^{55}$Mn, $^{162}$Dy, $^{52}$Cr, and $^{56}$Fe.

9. The method of claim 7, wherein said detecting is by magnetic resonance imaging or positron emission tomography.

10. The method of claim 1, wherein said administration is parenteral.

11. The method of claim 10, wherein said parenteral administration is by intradermal, subcutaneous, intramuscular, intraperitoneal, or intravenous injection.

12. The method of claim 10, wherein said administration is by gradual perfusion.

13. The method of claim 12, wherein said gradual perfusion is by intravenous or peristaltic means.

14. A method of detecting the underlying cause of an inflammatory response in vivo in an individual which comprises:

(a) administering to said individual a diagnostically effective amount of *a first agent, wherein said first agent comprises* a detectably labeled, *non-specific* immunoglobulin or [a] *an Fc* fragment *or subfragment* thereof, *and* wherein said immunoglobulin *or Fc fragment or subfragment* substantially accumulates at said site when said site is inflamed;

(b) imaging said individual to detect the presence of a site of inflammation;

(c) based on the presence of a site of inflammation as demonstrated by step (b), further administering to said individual a diagnostically effective amount of a detectably labeled specific antibody or a fragment thereof, wherein said detectably labeled specific antibody *or fragment thereof* can *specifically* bind to the underlying cause of the inflammatory response; and (d) imaging said individual to detect the presence of the detectable labeled specific antibody or fragment thereof bound to the underlying cause of the inflammation at the site of the inflammation.

15. The method of claim 14 which further comprises: treating the underlying cause of the inflammatory response therapeutically with an appropriate agent.

16. The method of claim 15, wherein said treating utilizes a therapeutically labeled antibody specific for said underlying cause of the inflammatory response, bound to said agent.

17. The method of claim 14, wherein said specific antibody is [monoclonally derived] *a monoclonal antibody*.

18. The method of claim 15, wherein said specific antibody is [polyclonally derived] *a polyclonal antibody*.

19. The method as in any one of claims 15–16, wherein said agent is a drug.

20. The method as in any one of claims 15–16, wherein said agent is a lectin.

21. The method of claim 20, wherein said lectin is the alpha-chain of ricin.

22. The method as in any one of claims 15–16, wherein said agent is a toxin.

23. The method of claim 22, wherein said toxin is diphtheria toxin.

24. The method as in any one of claims 15–16, wherein said agent is a radioactive isotope.

25. The method of claim 24, wherein said radioactive isotope is selected from the group consisting of $^{125}I$, $^{131}I$, $^{90}Y$, $^{67}Cu$, $^{217}Bi$, $^{211}At$, $^{212}Pb$, $^{47}Sc$, or $^{109}Pd$.

26. The method as in any one of claims 15–16, wherein said agent is an antimicrobial.

27. The method of claim 26, wherein said antimicrobial is selected from the group consisting of an anti-bacterial, an anti-fungal, an anti-viral, and an anti-parasitic.

28. The method of claim 1 or 14, wherein said individual is a human.

29. The method of claim 1 or 14, wherein said inflammation is a result of a microbial infection, a viral infection, a trauma, an autoimmune process, or a tumor.

*30. A method of detecting an inflammation site in vivo in an individual which comprises:*

*(a) administering to said individual a diagnostically effective amount of an agent wherein said agent comprises a detachably labeled immunoglobulin or an Fc fragment or subfragment thereof, and said immunoglobulin, or Fc fragment or subfragment thereof, substantially accumulates at said site when said site is inflamed wherein said accumulation is substantially independent of the epitopic specificity of the immunoglobulin; and*

*(b) detecting said agent.*

*31. The method of claim 30, wherein said agent is one or more detectably labeled monclonal antibodies.*

*32. The method of claim 3, wherein said one or more detectably labeled monoclonal antibodies are murine monoclonal antibodies.*

*33. The method of claim 17, wherein said monoclonal antibody is a murine monoclonal antibody.*

*34. The method of claim 31, wherein said monoclonal antibody is a murine monoclonal antibody.*

* * * * *